United States Patent [19]

Braun

[11] Patent Number: 4,588,461

[45] Date of Patent: May 13, 1986

[54] PROCESS FOR PRODUCING A VESSEL PROSTHESIS

[75] Inventor: Bernd Braun, Melsungen, Fed. Rep. of Germany

[73] Assignee: Intermedient GmbH, Emmenbrucke, Switzerland

[21] Appl. No.: 681,101

[22] Filed: Dec. 13, 1984

[30] Foreign Application Priority Data

Dec. 16, 1983 [DE] Fed. Rep. of Germany ....... 3345513

[51] Int. Cl.$^4$ ............................................. B65H 81/00
[52] U.S. Cl. ................................... 156/143; 156/172; 156/305; 156/308.6
[58] Field of Search ............... 156/172, 171, 143, 144, 156/305, 308.6, 308.4; 3/1.4; 604/282

[56] References Cited

U.S. PATENT DOCUMENTS 2,108,013  2/1938  Fehr ................................... 156/172
4,306,318 12/1981  Mano et al. ............................. 3/1.4

FOREIGN PATENT DOCUMENTS 892980  4/1962  United Kingdom ..................... 3/1.4

Primary Examiner—Michael Ball
Attorney, Agent, or Firm—Kenyon and Kenyon

[57] ABSTRACT

To produce a vessel prosthesis, a hose (12) is wrapped with a reinforcing thread (13) to avoid bending and clogging of the vessel prosthesis. The reinforcing thread (13) is wound substantially tensionless on the soft hose (12) thus prohibiting wavy deformations inside the hose. To exclude prior to the solidification of the adhesive connection a displacement of the reinforcing thread (13) being bonded to the hose, a band-shaped spacer (14) is wound up together with the reinforcing thread (13) and removed subsequently.

11 Claims, 6 Drawing Figures

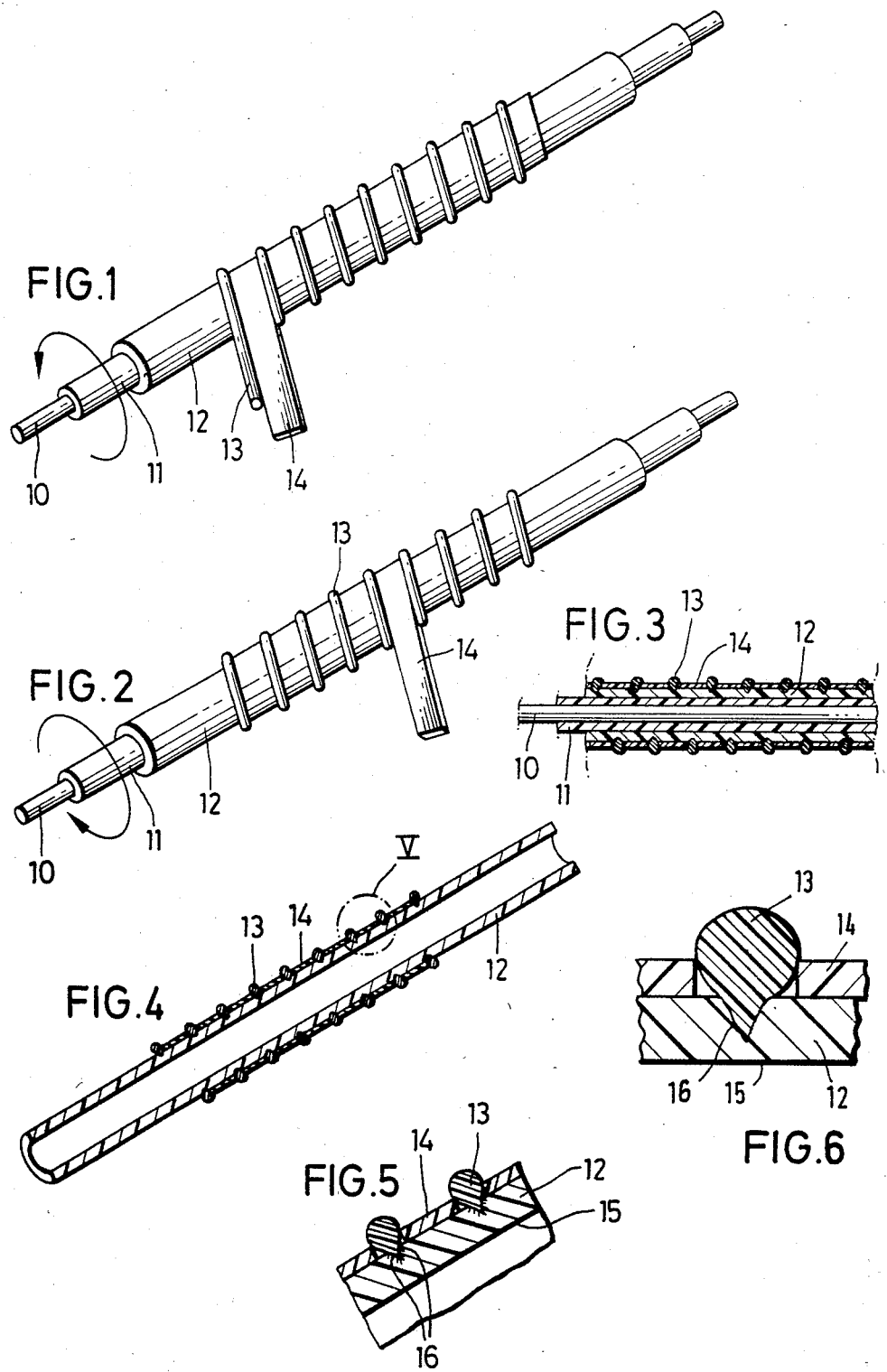

PROCESS FOR PRODUCING A VESSEL PROSTHESIS

The invention relates to a process for producing a vessel prosthesis, particularly a vessel prosthesis having a small diameter which can be used to replace blood vessels or vessel sections in a diseased or bad state. Up to now, vessel substitutes of a diameter of about 5 mm or less could be made but with partly satisfactory mechanical properties only, due to their insufficient resistance to bending not complying with the requirements to be fulfilled above all in the area of moving joints.

Prostheses of textile filaments, e.g. polyester filaments woven or knit according to textile-technical methods have been used successfully for some time in the surgical field for the vasculary replacement of original blood vessels. Their diameters are of 7 mm and more, corresponding to the venous or arterial blood vessels to be repaired, however, due to the insufficient stability, prostheses of a smaller lumen prepared according to the same process with diameters of less than about 4 mm may not be used successfully above all in the area and under the action of moving joints. Usually, porous vessel prostheses also including the textile prostheses mentioned above are sealed against the blood flowing in them by being impregnated with blood prior to their implantation so that the blood clotted in the interspaces, first forms a sufficiently dense layer. The coagulation layer consisting mainly of fibrin may have a thickness of between 0.5 to 1.5 mm. In case of smaller diameters, a layer of this thickness may contribute to a soon occlusion thus impairing the successful implantation of the vessel substitute.

With prostheses having a small lumen, a generally smooth inner surface of a uniform cross section counteracting the formation of fibrin and its addition is desirable. Prostheses of a corresponding density e.g. of polytetrafluoroethylene or non-woven-type materials need not be sealed by clotted blood, but they may be implanted readily without further measures. Substantially tight prostheses consisting of hidden polytetrafluoroethylene are for instance disclosed in German Auslegeschrift No. 27 02 513. The production of a microporous, non-woven material-type vessel prosthesis is explained in German Pat. Appln. No. 28 06 030, according to which, from a polymeric solution, e.g. a solution of a polyurathane built up of aliphatic or aromatic isocyanates and a polyol component, in tetrahydrofurane or dimethyl formamide fibers are prepared by spinning to obtain therefrom the prosthesis which, due to the oriented fibers is flexible in length and width and the tensile strength of which also corresponds to or even exceeds that of a natural blood vessel. However, the textile-technical prosthesis structure does not ensure the resistance to bending to the required extent in practical use with the necessary wall thicknesses of about 0.5 mm. Therefore, they do not lend themselves to prostheses to extend above or beneath joints, e.g. knee or elbow joints.

Flexible, tubular structures of braided textile material or of massive plastics often tend to fold aleady in case of slight curves so that the passage cross section will be strongly reduced. Further, folding sometimes entails irreversible material deformations resulting in a permanent wall damage. To correct this undesired behaviour with simple means, it has been known to wrap a resilient hose with a helically extending, rigid, flexible reinforcing thread and to thermally weld said thread to the hose surface. Instead of a continuous helical support, a number of reinforcing threads may be provided in the form of mutually spaced circular rings to stabilize the hose.

With vessel prostheses of a small lumen having wall thicknesses of about 0.5 mm only, the enveloping reinforcing thread causes by its inherent tension a deformation of the primarily smooth prostheses surfaces and the formation of groove-type impressions inside and outside. Such structures being integrated later in the tissue by growth are unimportant in regard to the outside. What is more critical and undesired accordingly is the formation of wavy or grooved surfaces on the prosthesis inside because the optimum linear blood flow will be affected by turbulences thus resulting finally in an increased deposition of thrombozytes, formation of thrombes and occlusion of the vessel.

In a known process for producing an implant, e.g. a vessel prosthesis, (German Patent Application No. 15 66 319), a cylindrical hose of a wide-meshed fiber material is slipped on a mandrel to be helically wrapped with a plurality of reinforcing threads which, by a subsequent thermal treatment, are fused with the hose whereby the fusing areas extend as far as to the hose inside involving the risk that a wavy strucutre is imparted to said hose inside.

Further, there has been known a vessel prosthesis of an accordion-type hose (DE-OS No. 21 52 142). A reinforcing thread is wrapped detachably into the helically extending hose folds, the hose inside of said vessel prosthesis being always wavy.

It is the object of the invention to provide a process allowing to produce bending-resistant vessel prostheses without a structural deformation of the hose inside. Said problem may be solved in that with the winding of the reinforcing thread, the hose wall and, above all, its inside are not deformed such as to result in an uneven and wavy surface.

According to the process of the invention, a practically tensionless winding support causing no surface deformation, and being firmly connected to said surface is applied to the hose surface. The prosthesis section present on a rod-shaped support and having a wall thickness of preferably 0.5 to 0.6 mm is caused to rotate thus winding loosely around the hose the reinforcing thread which preferably consists of a material having the mechanical properties of the material of the hose. In case of a polyurethane hose, a corresponding polyurethane thread made of a thermoplastic polyurethane of a Shore hardness A 70 to 90 and having a diameter of 1 mm as well as a tensile strength of about 20 N would be useful to this effect. For a power-transmissive connection of polyurethane wire and prosthesis surface, use is made of the property of the utilized polyurethanes that they may be partially dissolved to be bonded together under the action of specific solvents such as tetrahydrofurane or dimethyl formamide. Prior to contacting the prosthesis surface, the polyurethane wire is wetted with the solvent. This is generally sufficient for the desired bonding. Within the scope of the invention, it is also possible to thermally melt or weld the reinforcing thread to the hose with the proviso that the melt ranges have to end at a distance from the hose inside.

As explained above, to avoid deforming of the prosthesis, the supporting wire coil should be applied free of tension and without any pressure to the prosthesis surface. Even with a substantial reduction of the wire tension during the winding operation, it is not possible to effect bonding without any contact pressure. In view of the circular cross section of the wire, its contact surface with the hose is small, thus bringing about a high specific surface contact pressure with a given tension, so that the mentioned procedure will not serve the desired purpose. To exclude undesired effects on the hose, it is additionally suggested to wind up in common with the reinforcing thread forming the coil and being bonded, a non-bonding band extending in parallel and determining the distance between the wire turns, i.e. the winding interspaces. Due to said band, or tape, the reinforcing thread may be wrapped around the hose surface at a low pressure and with a lateral guidance and support, and its windings cannot be displaced either. As a result of the concomitantly applied band, the prosthesis surface by itself is stabilised and a uniform distribution of forces is ensured simultaneously. Preferably, the band is made of a material being inert against the solvent used for the bonding between the polyurethane wire and the prosthesis surface. To this effect, polymerized fluorocarbons such as polytetrafluoroethylene and polyethylene, polypropylene are particularly suitable.

Upon the application of the parallel winding, the solvent is removed at 40° to 50° C. and the auxiliary band wrapped concomitantly is taken off to leave the reinforcing thread bonded firmly meanwhile to form a unit with the hose surface.

A preferred embodiment of the invention will be explained hereinafter in more details with reference to the drawings.

FIG. 1 is a perspective view showing the winding of the reinforcing thread together with the band-shaped spacer on the hose, FIG. 2 shows the unwinding of the spacer from the vessel prosthesis, FIG. 3 is a longitudinal section of FIG. 1, FIG. 4 is a longitudinal section of the vessel prostheses without the mandrel, FIG. 5 is a scaled up view of the detail V of FIG. 4 and FIG. 6 is a scaled-up view of the cross section of the bonding point between reinforcing thread and hose such as seen by inspection with the electron scan microscope.

According to FIG. 1, a rotatably supported mandrel 10 in the form of a metallic rod is provided with a plastic sheathing 11 of polyethylene which, in turn, is enclosed by a hose 12 formed by a plurality of wound polyurethane threads, according to the process of DE-OS No. 28 06 030. FIG. 1 shows the process subsequent to the cross-linking of the hose 12 which, while being left on the plastic sheating 11 on which it had been made, is provided with a reinforcing thread 13 and with a band-shaped spacer 14 wound side-by-side on said hose to produce a helical coil in which the individual windings of the reinforcing thread 13 are separated from one another by a respective winding of the band-shaped spacer 14. Prior to the application of the reinforcing thread 13 to the hose 12, its underside will be coated with a solvent. The material polyurethane forming the reinforcing thread 13 is identical to that of the hose 12, while the spacer 14 consists for inst. of polyethylene which is inert against the used solvent. The reinforcing thread 13 is wound at an extremely low tension thus enabling it to rest loosely on the surface of the hose 12 which will not be substantially impressed by it. The cross section of the reinforcing thread 13 is circular. Its underside contacts nearly linearly the hose. Due to the solvent, the underside of the reinforcing thread 13 and the contact area of the hose 13 with the former are partially dissolved to result in a bonding between the reinforcing thread and the hose 12 without substantial impressions by the individual windings in the hose surface. During the winding operation, the spacer 14 is responsible for preventing the loosely applied windings of the reinforcing thread 13 from sliding on the hose 12.

If the reinforcing thread 13 is bonded with hose 12, the solvent is removed e.g. by evaporation. Subsequently, the mandrel 10 is turned in counterdirection for the winding operation, the band-shaped spacer 14 being unwound from the hose 12. (FIG. 2). The vessel prosthesis which is now finalised may be removed from the mandrel 10 in that the ends of the plastic sheathing 11 are torn apart thus, due to the transverse contraction of the plastic sheathing, causing a reduction of its outer diameter so that the hose 12 may be removed axially from the mandrel 10.

The final vessel prosthesis made of soft-flexible polyurethane has a smooth inside free of any wavy impressions from the reinforcing thread 13 thus reducing the risk of blood flow turbulences in the vessel prosthesis. However, the underside of the reinforcing thread 13 is firmly connected to the hose 12 at the bonding points 16 filling partly the wedge-shaped gaps beneath the reinforcing thread 13. As obvious from FIGS. 3 to 6, the windings of the reinforcing thread 13 laterally rest on the outer edges of the spacer 14 thus reducing the contact area between the hose 12 and the reinforcing thread 13 which is only in quite a loose contact with the hose. FIG. 6 shows that the solvent does not only enter the lower region of the reinforcing thread 13 but also the outer area of the hose 12. Further, FIG. 6 allows to note the consequences of a certain partial solution and compacting of the prosthesis material where the winding is bonded which, however, does not extend as far as to the inside 15; impressions extending to the inside 15 are also avoided with the use of a reinforcing thread 13 of a round cross section and of a narrow support surface. However, it is also possible to use a non-circular reinforcing thread having a larger support surface.

It is not absolutely necessary to use one sole reinforcing thread 13 which is wound up helically. One also may provide a multiple winding of a plurality of reinforcing threads and of several band-shaped spacers. Further, it is possible to slip on the hose 12 individual circular rings of one reinforcing thread each and to use annular spacers 14 to keep said rings in spaced relationship.

What is claimed is:

1. A method for producing a vessel prosthesis that is resistant to bending and possesses a smooth interior, which comprises the following steps:
   (a) covering a mandrel with a cylindrical hose having a smooth interior;
   (b) winding at least one reinforcing thread and a band-shaped spacer around said hose with individual windings of said thread separated by windings of said band-shaped spacer so that said thread rests loosely but stably on said hose with said interior of said hose remaining smooth; then,
   (c) bonding said thread to said cylindrical hose so that said interior of said hose remains smooth; then,
   (d) removing said band-shaped spacer; and then,
   (e) removing said cylindrical hose with said thread bonded thereto from said mandrel.

2. A method as in claim 1, wherein step (c) includes welding said reinforcing thread to said cylindrical hose.

3. A method for producing a vessel prosthesis that is resistant to bending and possesses a smooth interior, which comprises the following steps:
 (a) covering a mandrel with a cylindrical hose having a smooth interior;
 (b) coating an underside of at least one reinforcing thread with a solvent of said thread and said hose so that when said thread is loosely wound around said hose said thread and said hose are dissolved at areas of contact without substantially affecting said interior of said hose; then,
 (c) winding said thread and a band-shaped spacer around said hose with individual windings of said thread separated by winding of said band-shaped spacer so that said thread rests loosely but stably on said hose with said underside of said thread in contact with said hose, and said interior of said hose remaining substantially smooth; then,
 (d) evaporating said solvent; then,
 (e) removing said band-shaped spacer; and then,
 (f) removing said cylindrical hose with said thread bonded thereto from said mandrel.

4. A method as in claim 3 wherein step (a) includes forming said cylindrical hose on said mandrel from a plurality of threads.

5. A method as in claim 4 wherein said cylindrical hose comprises polyurethane, and said reinforcing thread comprises polyurethane.

6. A method as in claim 4 wherein step (a) further includes initially slipping a flexible sheathing on said mandrel, and wherein step (f) includes stretching said flexible sheathing longitudinally so that an outer diameter of said flexible sheathing is reduced.

7. A method as in claim 6 wherein said cylindrical hose comprises polyurethane, and said reinforcing thread comprises polyurethane.

8. A method as in claim 3 wherein step (a) includes initially slipping a flexible sheathing on said mandrel, and wherein step (f) includes stretching said flexible sheathing longitudinally so that an outer diameter of said flexible sheathing is reduced.

9. A method as in claim 8 wherein said cylindrical hose comprises polyurethane, and said reinforcing thread comprises polyurethane.

10. A method as in claim 3 wherein said cylindrical hose comprises polyurethane, and said reinforcing thread comprises polyurethane.

11. A method as in claim 3 wherein said band-shaped spacer comprises a material inert to said solvent.

* * * * *

UNITED STATES PATENT AND TRADEMARK OFFICE
CERTIFICATE OF CORRECTION

PATENT NO. : 4,588,461

DATED : May 13, 1986

INVENTOR(S) : Bernd Braun

It is certified that error appears in the above-identified patent and that said Letters Patent is hereby corrected as shown below:

Column 1, line 32, between "may" and "contribute", insert --soon--.

Column 1, line 32, delete the second "a" and substitute therefor --an--.

Column 1, line 33, delete "soon".

Column 1, line 62, delete "aleady" and substitute therefor --readily--.

Column 2, line 17, delete "thrombes" and substitute therefor --thrombus--.

Column 2, line 33, delete "allowing to produce" and substitute therefor --for producing--.

Column 2, line 53, delete "prothesis" and substitute therefor --prosthesis--.

UNITED STATES PATENT AND TRADEMARK OFFICE
CERTIFICATE OF CORRECTION

PATENT NO. : 4,588,461

DATED : May 13, 1986

INVENTOR(S) : Bernd Braun

It is certified that error appears in the above-identified patent and that said Letters Patent is hereby corrected as shown below:

Column 3, lines 38-39, delete "prostheses" and substitute therefor --prosthesis--.

Column 3, line 52, delete "sheating" and substitute therefor --sheathing--.

Column 3, line 62, delete "inst." and substitute therefor --instance--.

Column 5, line 13, between "said hose" and "said thread", insert --,--.

Signed and Sealed this

Fourteenth Day of March, 1989

Attest:

DONALD J. QUIGG

Attesting Officer

Commissioner of Patents and Trademarks